(12) United States Patent  
Moonay (10) Patent No.: US 7,207,210 B2  
(45) Date of Patent: Apr. 24, 2007

(54) MULTI-DECADE VISCOMETRIC OR RHEOLOGIC MEASUREMENTS OF A MATERIAL UNDERGOING STATE CHANGE

(75) Inventor: David J. Moonay, Stoughton, MA (US)

(73) Assignee: Brookfield Engineering Laboratories, Inc., Middleboro, MA (US)

( * ) Notice: Subject to any disclaimer, the term of this patent is extended or adjusted under 35 U.S.C. 154(b) by 145 days.

(21) Appl. No.: 10/962,104

(22) Filed: Oct. 8, 2004

(65) Prior Publication Data

US 2006/0075805 A1 Apr. 13, 2006

(51) Int. Cl.  
*G01N 11/14* (2006.01)

(52) U.S. Cl. .................... 73/54.28; 73/54.31

(58) Field of Classification Search .......... 73/54.28, 73/54.31, 54.32, 54.33, 54.34  
See application file for complete search history.

(56) References Cited

U.S. PATENT DOCUMENTS

| | | | | |
|---|---|---|---|---|
| 4,299,119 A | * | 11/1981 | Fitzgerald et al. | 73/54.28 |
| 4,448,061 A | | 5/1984 | Brookfield | 73/54.33 |
| 5,167,143 A | | 12/1992 | Brookfield | 73/54.23 |
| 5,503,003 A | | 4/1996 | Brookfield | 73/54.32 |
| 6,463,793 B1 | | 10/2002 | Selby | 73/54.28 |

* cited by examiner

*Primary Examiner*—Daniel S. Larkin  
(74) *Attorney, Agent, or Firm*—Burns & Levinson, LLP; Jerry Cohen (57) ABSTRACT

Range-extending method and apparatus for testing the viscosity of a fluid (10) undergoing a state change utilizing a viscometer (2) with a rotary assembly (42) for measuring, by automatically changing the rotational speed of the rotary assembly in response to measuring a torque or other test parameter when it meets a target torque trigger and/or other test parameter threshold.

28 Claims, 14 Drawing Sheets

MULTI-DECADE VISCOMETRIC OR RHEOLOGIC MEASUREMENTS OF A MATERIAL UNDERGOING STATE CHANGE

FIELD OF THE INVENTION

The present invention relates generally to rheological and viscometric measurements, and more specifically to measurements of materials undergoing physical state changes, and which may be employed for laboratory research and/or industrial process quality control purposes.

BACKGROUND OF THE INVENTION

Many rheological instruments have been too complex and too expensive to meet the full needs of industrial process users and laboratory users. Also, past designs have not been adaptable to the variety of tests required by users, thereby forcing the purchase of several pieces of equipment, impracticably expensive equipment, or limitations in testing capability.

The state of the art of more affordable viscometry involves a calibrated application of shear force to a fluid to be tested and measuring torque and/or time-to-torque of the shear resistance of the fluid (its viscosity). Standard Scanning Brookfield techniques are well known in the field of viscometry and rheology. See, e.g., ASTM D 5133-96; See also, e.g., prior U.S. Pat. No. 3,886,789 (Jun. 3, 1975) of Donald W. Brookfield and U.S. Pat. No. 4,175,425 (Nov. 27, 1979) and U.S. Pat. No. 5,167,143 (Dec. 1, 1992) of David A. Brookfield, all of common assignment with the present application and the contents of which are incorporated by reference as though spelled out at length herein. See also the references cited in said prior patents.

There are many materials whose viscosity changes during processes of thermo-reversible gelation or chemical gelation (chemical cross-linking.) Such materials include, for example, gelatin, curable epoxies, certain lubricants, and mixtures of synthetic polymers and solvents. When such materials undergo state changes, their viscosities can change up to four or five decades (orders of magnitude.) Generic gel timers provide no viscosity data to laboratory personnel. Such personnel who wish to acquire viscosity data throughout the entire gelation process are required to conduct numerous separate measurements requiring careful process parameter definitions.

Thus, it would be useful to provide affordable instrumentation and a method for automatically measuring multiple decades of apparent viscosity changes in a material as it undergoes a state change such as occurs in thermo-reversible gelation or chemical gelation.

SUMMARY OF THE INVENTION

The present invention addresses the needs described above by extending the range of measurements automatically taken using a relatively simple, rotary viscometric or rheometric instrument.

The present invention provides, in one aspect, a method of measuring a physical property such as, for example, a viscometric or rheologic property, of a fluid undergoing a state change (e.g., gelation or crystallization), through use of a rotary viscometric or rheometric instruments having a spindle, a sample chamber for holding the fluid into which the spindle is to be immersed, a calibrated spring or other means for adjustably driving the spindle at different speeds, and a rotary variable displacement transducer or similar means for monitoring drag on the spindle (i.e., an increase in viscosity will be indicated by an increase in spring deflection) and converting the monitored drag into a torque measurement.

In one embodiment, the instrument employed is a Brookfield-type viscometer or rheometer having programmable test process parameters, such as the DV-II+ Programmable, DV-II+ Pro, DV-III+, or DV-III Ultra manufactured by Brookfield Engineering Laboratories™. The invention does not, however, require usage of these particular programmable instruments, whose operation can be controlled with well established scripting languages. A fluid sample undergoing or to undergo a state change is placed in the sample container, which preferably has integrated fluid temperature monitoring and control capabilities. The spindle is then immersed into the fluid. The spindle is then rotated at a constant rotational speed, and the torque imparted to the spindle is measured. As the fluid sample changes states, the torque imparted will either increase (e.g., if the sample is gelling) or decrease (e.g., if the sample is, for example, being heated or otherwise caused to de-gel.) The torque measurements continue until at least one "target torque" set point is reached. Upon reaching this set point, a determination whether the testing should continue is made based upon whether one or more process parameters (e.g., time, final torque, etc.) has reached their respective, predefined end point. The torque (and other process parameter) measurements continue in an iterative manner, with dynamic changes of the spindle rotational speed commensurate with the viscosity changes of the fluid sample, until one or more of the predefined process parameter end point(s) are reached.

The "target torque" set point is preferably defined in terms of a percentage of the instant full scale range (FSR) of the viscometer instrument employed. In some embodiments, for example, the set points are fixed at 10% or 90% FSR depending upon whether the test involves decreasing or increasing sample fluid viscosity. If, for example, the sample fluid's viscosity is increasing throughout the testing, the rotational speed will be automatically reduced by some predetermined factor to a lower constant rotational speed in order to preserve accurate measurements in a calibrated range and prevent damage to the measuring instrument. In a preferred method, the spindle rotational speed is dynamically reduced one decade (to 10% of original) when the measured apparent viscosity reaches a 'target torque' of 90% FSR of the instrument. This adjustment is repeated each time the apparent viscosity reaches the 'target torque' of 90% FSR, until a test end point is indicated. The converse approach to testing is also possible, whereby the rotational speed of the spindle is increased commensurately (e.g. by a decade) with attainment of a lower 'target torque' (e.g., 10% of FSR) for fluid samples whose viscosity is decreasing through the testing.

In another aspect, the present invention provides a range-extending improvement over existing rotary viscometers and rheometers that includes a control means for accepting at least one target torque set point and/or end point process parameter, automatically (i.e., without user intervention) effecting the change in the rotational speed of the spindle when the at least one target torque set point is attained, and stopping the test when one of the end points is reached.

The invention provides an automated, reliable test that can be performed utilizing less costly instrumentation and that accommodates multi-decade (e.g., four to five decades) apparent viscosity changes in various materials undergoing state changes. In Brookfield-type rotary viscometers having programmable capabilities, the control means comprises an algorithm supplementing the instruments' automated data acquisition and control system, that will prove useful to laboratories of various industries desiring to automate their monitoring of gelation or crystallization, but which cannot afford more expensive or exotic equipment. Furthermore, this is a significant improvement over existing low-cost methods, such as "torsion gelometers" that only provide gel times but no rheometric data The invention is not, however, limited to programmable rotary viscometers, as the control means could just as easily be implemented by an external general purpose computer executing the algorithm described below and receiving input from a non-programmable viscometer and providing responsive control signals to, for example, the motor driving the rotary viscometer spindle/rotor.

BRIEF DESCRIPTION OF THE FIGURES OF THE DRAWING

For a better understanding of the present invention, together with other and further objects thereof, reference is made to the accompanying drawings and detailed description, wherein.

DETAILED DESCRIPTION OF PREFERRED EMBODIMENTS OF THE INVENTION

Figure 1:
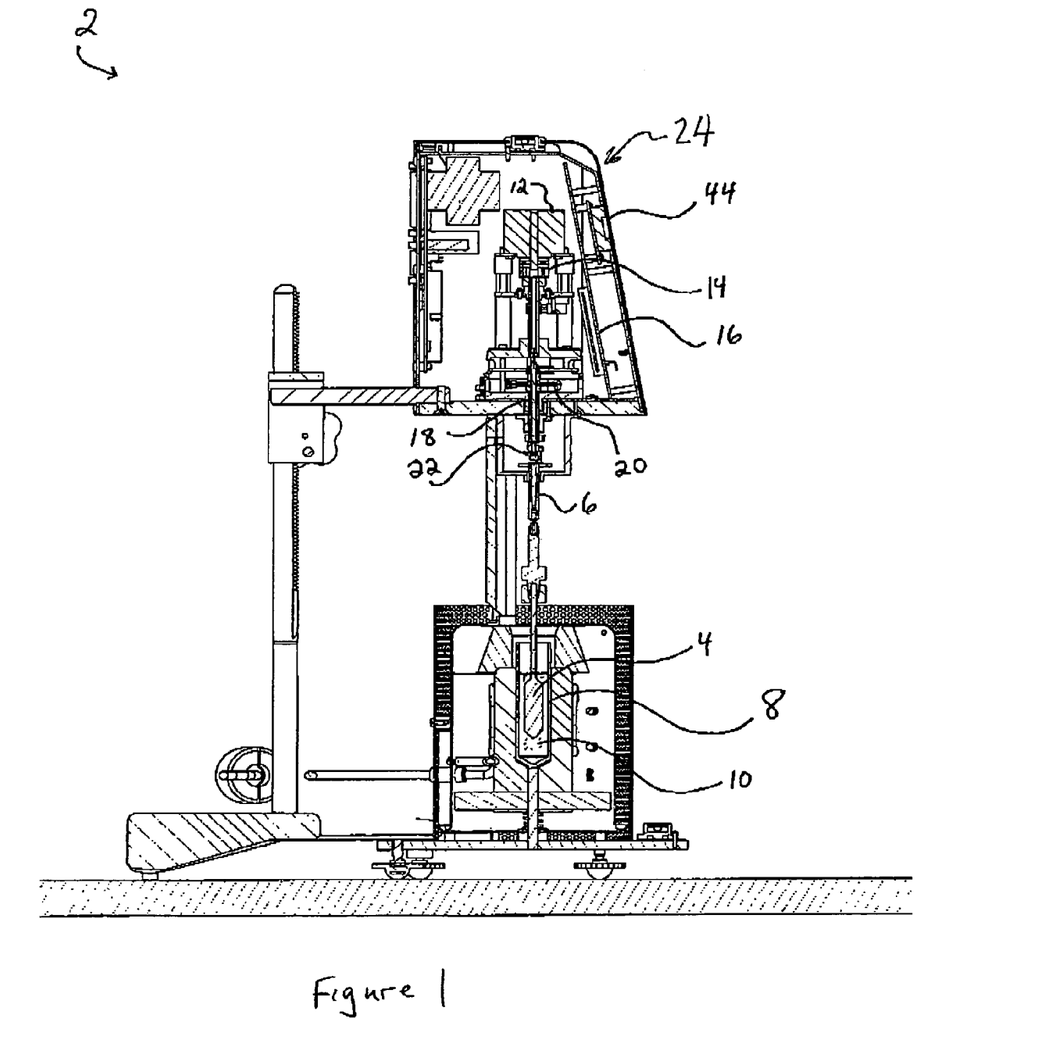
FIG. 1 is a cross-sectional view of a preferred Brookfield-type viscometer equipped with a logic unit in accordance with an embodiment of the present invention.

With reference to FIG. 1, the present invention provides a system and method for measuring the viscosity of a material undergoing a state change and utilizes rotary viscometers and similar instruments, such as the Brookfield DV-II+ Pro viscometer or others known in the art and referenced above. A rotary viscometer 2 is generally composed of several mechanical subassemblies, including a rotor (usually a vertically arranged spindle 4 suspended at an end of a supporting shaft 6), a sample chamber 8 for holding a fluid sample under test 10 into which the spindle 4 will be immersed, a drive motor 12 and coupling 14 providing multi-speed rotation controlled by a programmable logic unit (i.e., microprocessor 16.) The spindle 4 is rotated by the supporting shaft 6 and creates a torque loading (dependent on fluid viscosity) transmitted through the shaft to a transducer for generating an output reading or control signal. Torque is the shear stress as measured by a yielding coupling (e.g., a spring, high strength wire element, pivot shaft 18 etc.) that yields in response to stress encountered at the spindle 4 to establish a relative angular deflection continuously measurable by various forms of electrical, magnetic, optical, acoustic pick-ups well known in the art per se and convertible to a digital signal. The microprocessor 16 executing logical instructions dynamically adjusts the rotational speed of the rotor assembly based upon determinations whether the measured torque has achieved a torque set point (a "target torque".)

In the viscometer 2 shown, the sample chamber 8 defines precisely a cylindrical volume for containing the fluid sample 10. Any controlled volume could be employed, but preferably the sample chamber will either integrate or allow use with temperature monitoring and control components (not shown) in communication with and/or operable by microprocessor 16. A temperature probe (such, as a thermostat or other temperature responsive sensor) may be wired or connected via a communications port to a logic unit such as microprocessor 16.

The spindle 4 is mounted in an aligned position in the supporting assembly 6, which is driven by a pivot shaft 18, which is directly connected to the transmission (motor and gearing), through a jeweled bearing 22 that provides radial control and axial support, but allows rotation. A rotary transducer 20 that may comprise an industry standard electromagnetic (microsyn) pickup senses deflection in the pivot shaft 18 that results from drag imparted to the spindle 4 as it rotates in the fluid sample 10. The motor 12 and coupling 14 are mounted on fixed chassis structure 24 of the instrument. The motor 12 is typically a stepper motor or variable speed motor sufficient to drive against axial loads.

Shear forces imparted by the fluid sample 10 to the spindle 4 cause a deflection or twist of the pivot shaft 18 in an arc measurable by transducer 20. More angular deflection within a predefined full scale range allows greater sensitivity, but it is imperative to maintain the deflection well within the elastic range of the pivot shaft (or other element employed.)

Figure 2:
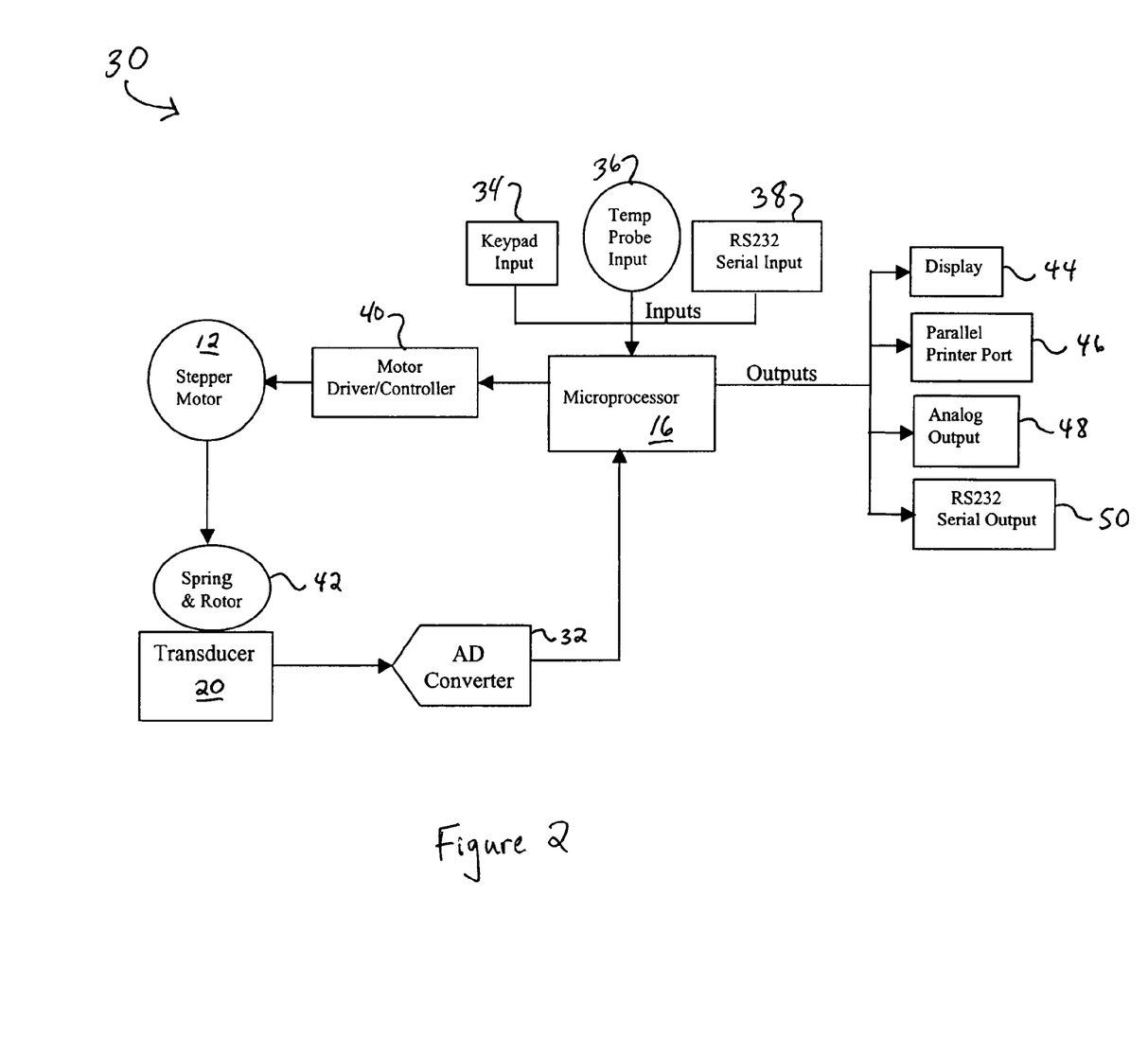
FIG. 2 is a schematic representation of the electrical system in a preferred viscometer in accordance with an embodiment of the invention.

FIG. 2 shows an electrical circuit 30 illustrating electrical and data communications between microprocessor 16 and other components of viscometer 2. The controller receives a number of inputs, including signals from transducer 20 (converted from analog to digital form by converter 32), data from a fluid temperature sensor 36, user inputs (e.g., program selection, operating parameters, etc.) through a keypad 34 and/or data from other equipment (possibly even including executable instructions) through a standard communications port 38. The speed at which motor 12 drives the rotating assemblies 42 (spring/pivot shaft 18 and rotor/spindle 4) is controlled by microprocessor 16 via motor driver/controller 40. Microprocessor 16 preferably conditions the input signals and makes them available at one or more output components, including display 44, printer port 46, analog output 48 and/or serial port 50. Measurement conditions and results, including time, temperature and viscosity readings may be viewed, recorded, printed, or used (in certain embodiments) for external process control.

In one aspect, the invention provides a control means for selecting one or more target torque set points, preferably in terms of a percentage of the instant FSR of the instrument, and a means for dynamically changing the rotational speed of the rotating assemblies when one or more of the target torque set points is achieved. The set points may be manually entered by the user at the time of testing, or alternatively may be stored in memory for retrieval with control logic executing on microprocessor 16. The control logic is responsible for receiving (or retrieving from memory) a variety of process control set points, process monitoring information and acquired data, redirecting and/or reformatting the information and data (e.g., for display devices and other peripheral equipment) and automatically generating instrument control signals responsive to the set points, monitoring information and acquired data. This logic is preferably implemented in executable software resident on microprocessor 16, however those of skill in the field could easily envision hardware implementations and/or designs wherein microprocessor 16 may not be an integral part of viscometer 2. The DV-II+ Pro and DV-III-series instruments, for example, may be operated remotely with bi-directionally (e.g., between a computer and the instrument via RS-232 serial connections) communicating control software such, as Rheocalc™. A function essential to the invention is the ability, however implemented, to allow dynamic (automatic) changes in the rotational speed of the spindle upon the occurrence of some pre-defined event.

In the Brookfield-type viscometers or rheometers listed above, microprocessor 16 is internal to the viscometer and is capable of executing customized test programs downloaded to the instrument from external sources via loading software (e.g., DV Loader™, Rheoloader™, Wingather™ or Rheocalc™.) In one embodiment, a microprocessor in accordance with the present invention can accept, for example, through the user interface keypad 34 a variety of process parameter set points and end points to: define automatic data acquisition intervals; to operate as triggers for dynamically changing the rotational drive speed; and/or to cease testing of a fluid sample. The test parameter set points may comprise target torque(s) expressed in terms of a percentage of full scale range, or time, temperature, shear rate, and shear stress thresholds, among others. As noted above, in alternative embodiments the set points and/or testing end points maybe stored in memory in retrievable files formatted for use by the loading software and/or the control program, or may comprise a portion of the control program itself.

Display and output of data acquired through viscometers including logic units in accordance with the present invention is somewhat like that of conventional affordable instruments, except the present invention vastly extends the range of such viscometers. The present invention allows one to measure vastly increasing or decreasing viscosities of fluids undergoing a state change, such as occur as a result of chemical gelation (e.g., epoxy setting or curing) or physical gelation (e.g., gelling of a gelatin in water during cooling.)

Figure 3:
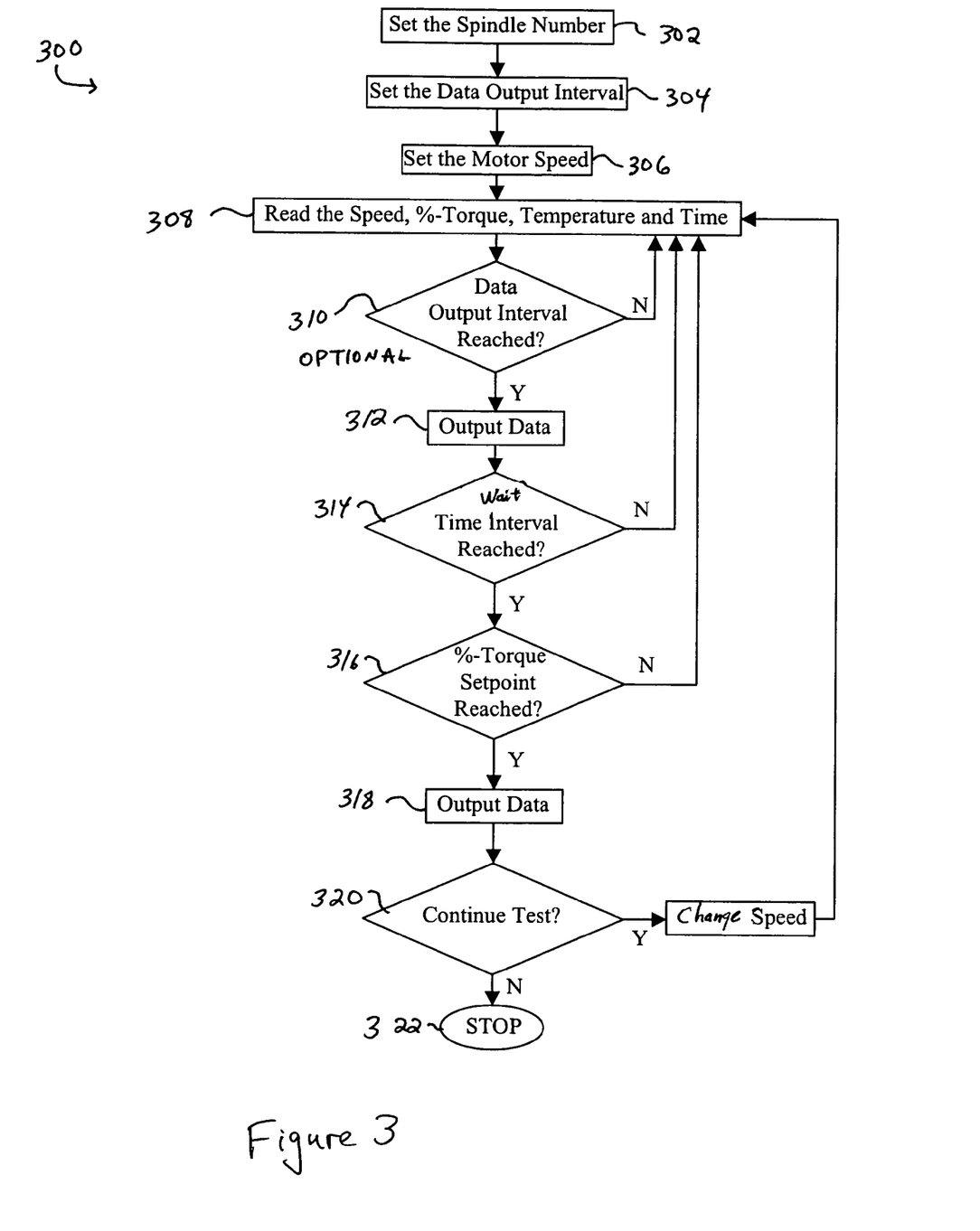
FIG. 3 is a state flow diagram of an algorithm representing steps of a method for extending the measurement range of the viscometer in accordance with an embodiment of the present invention.
Figure 4A:
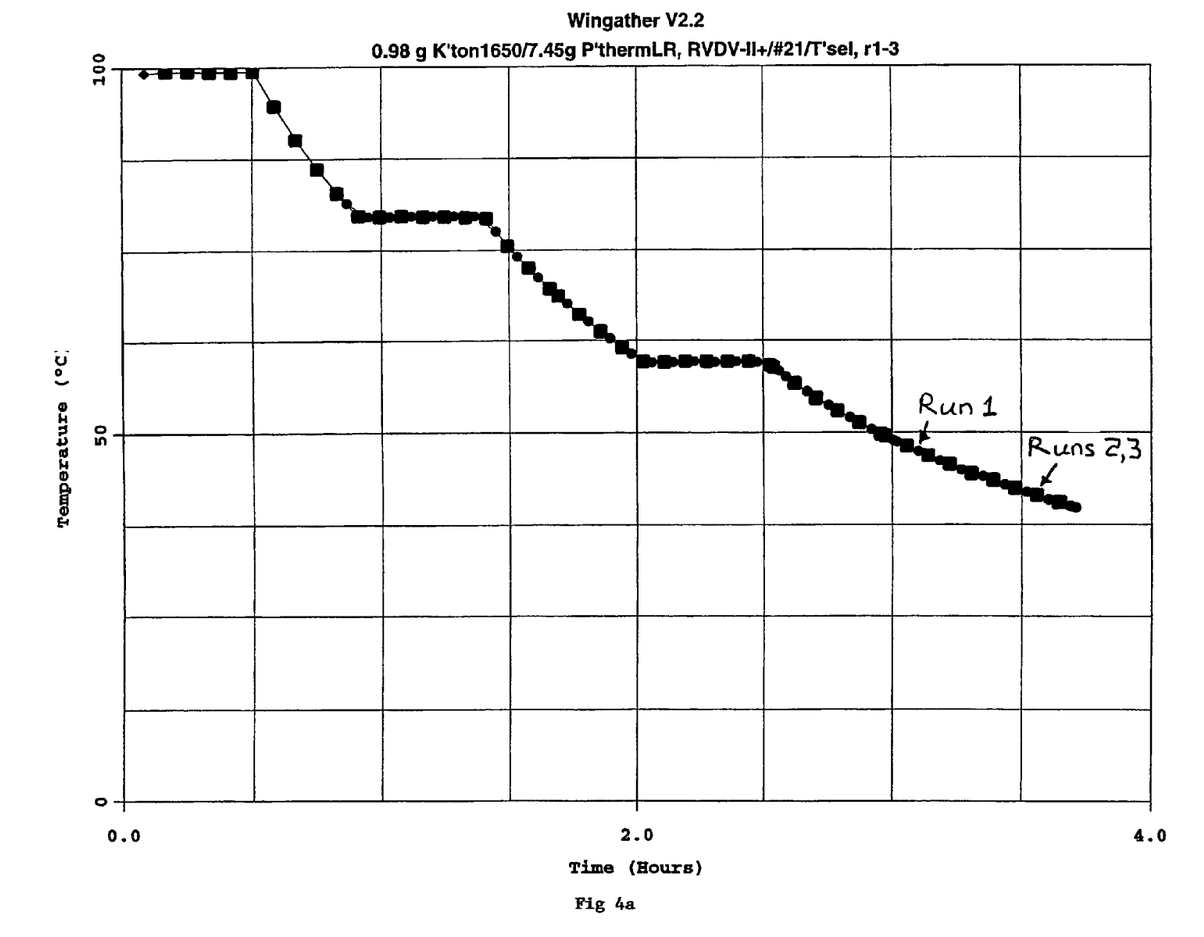
FIGS. 4A–4E are graphical representations of data acquired during the testing of a fluid sample per a method in accordance with an embodiment of the invention.
Figure 4B:
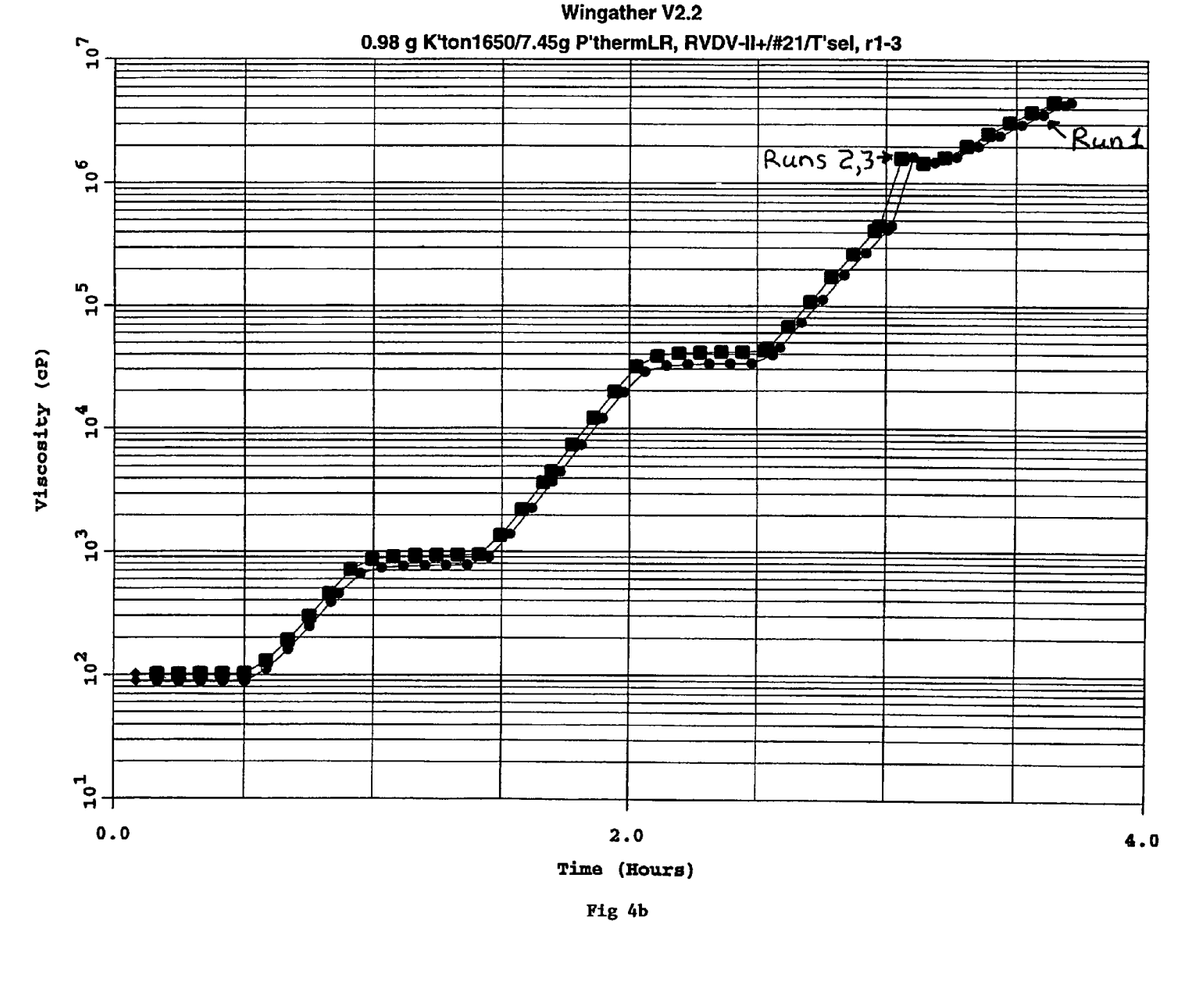
Figure 4C:
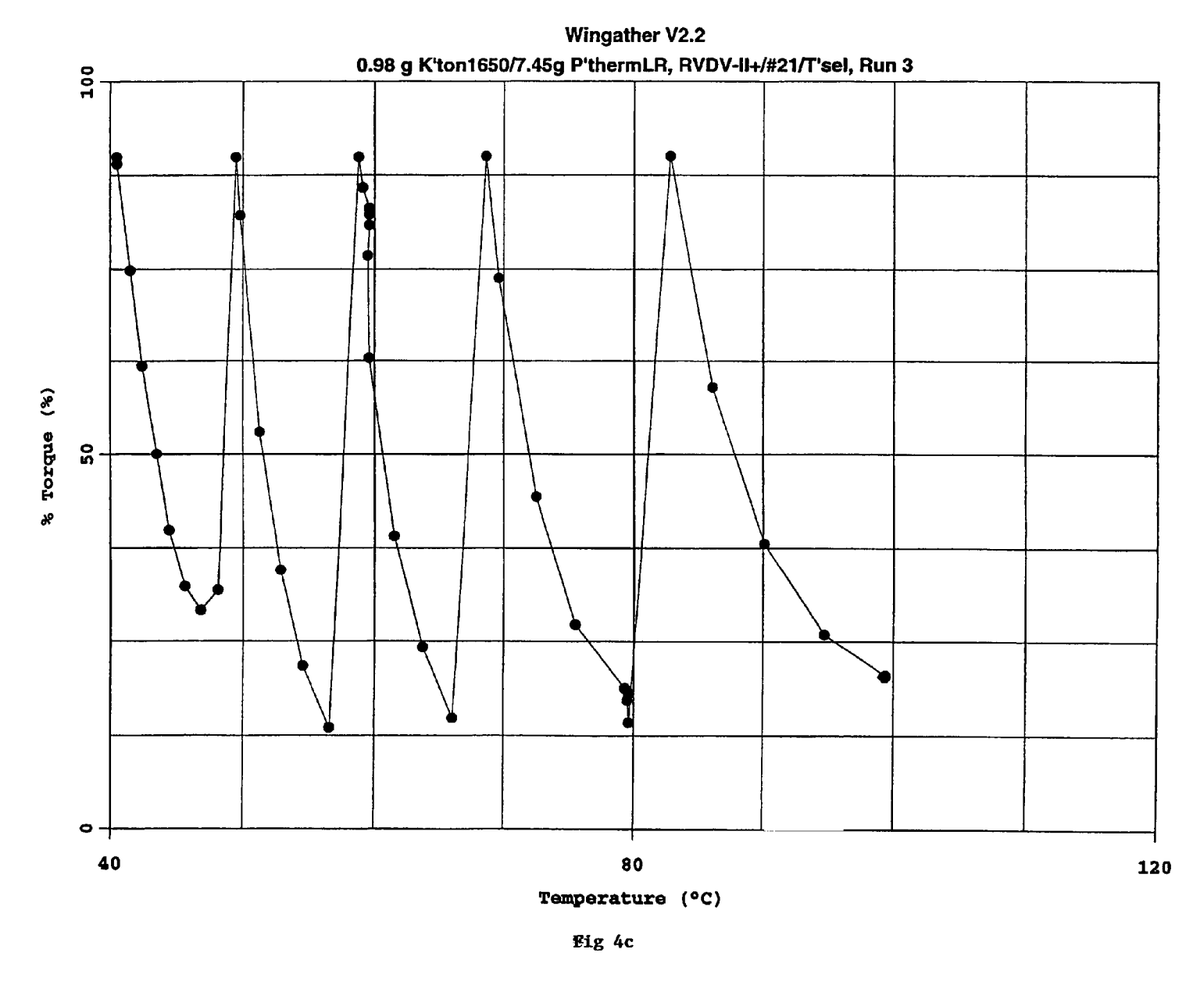
Figure 4D:
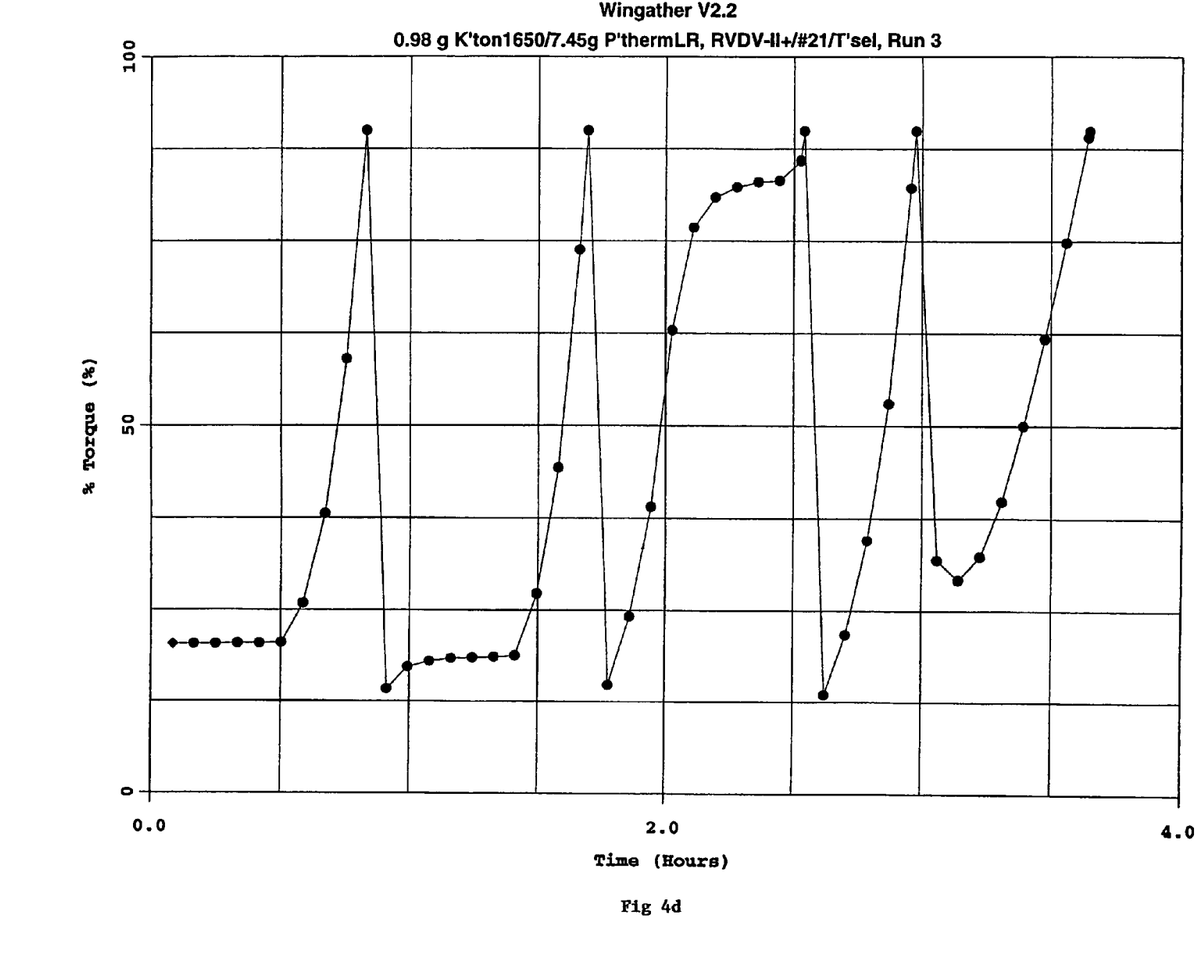
Figure 4E:
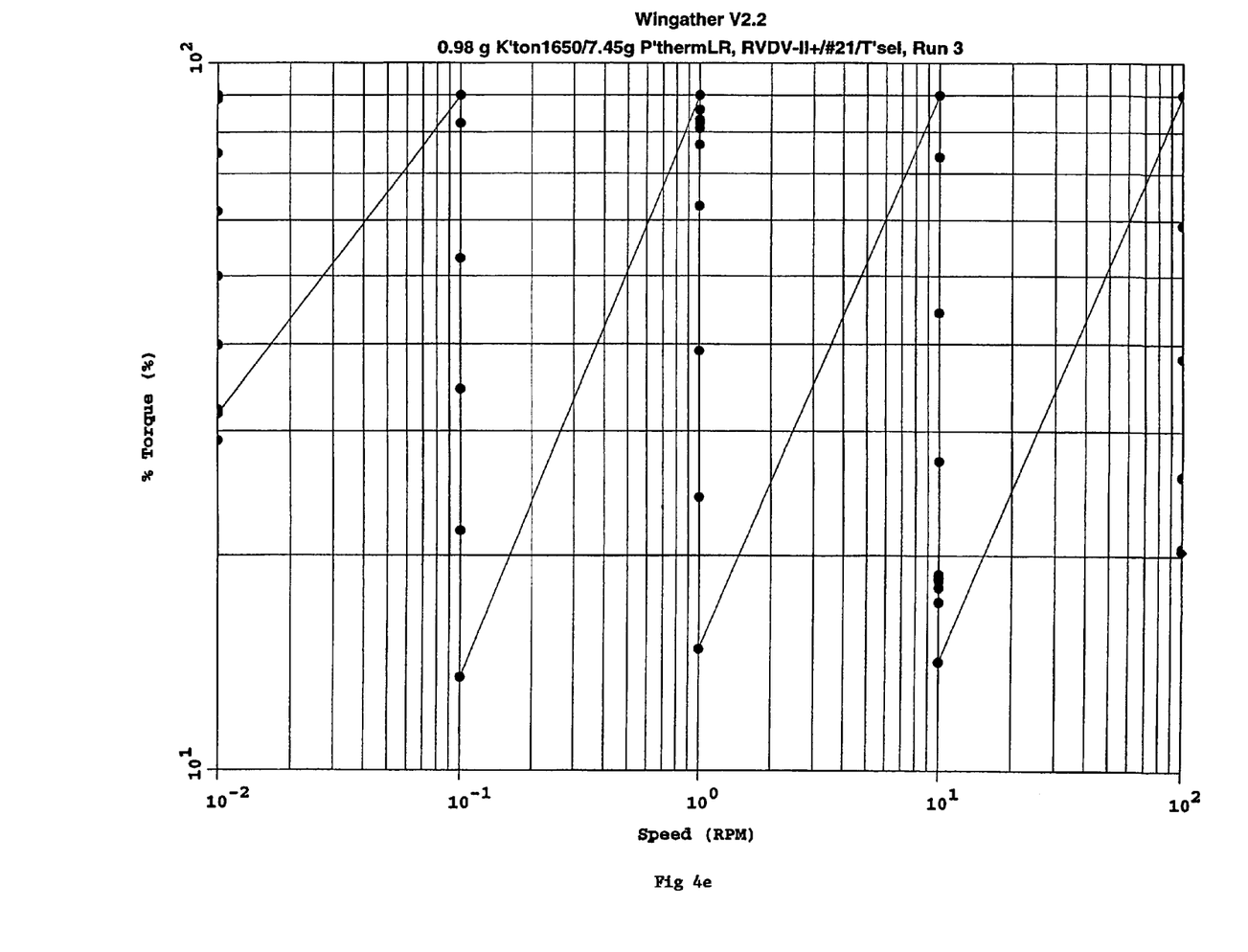

FIG. 3 shows a state flow diagram 300 of a program executed by microprocessor 16 for implementing the range-extending method of the present invention. Testing a substance throughout gelation may require half a day, less, or more. In steps 302–306, the values of certain operational parameters are initially set by the control program, preferably by retrieving such values from files stored in memory, however, the values could just as easily be embedded within the control program, or possibly even input via keypad by the instrument operator.) The parameters may include: spindle selection; the desired data output interval; an optional "wait time"; %-Torque set point (target torque trigger threshold); and an initial speed in the present configuration. Once all the initial processing conditions are set, the spindle is rotated at a first rotational speed through operation of the stepper motor.

The fluid sample 10 to be tested is provided to the sample chamber 8 in an amount suitable to allow immersion of the spindle 4. During the testing, transducer sensing of the torque imparted to the spindle is communicated to the microprocessor 16 for conversion to viscosity measurements and for display and/or recording. Other structural details of the rotary viscometer 2 are described above and/or are well known in the art. In the practice of the invention, the fluid sample may be subject to a temperature variation, typically as a lowering of the temperature by use of a cooling bath around the sample chamber 8. Temperature variations need not, however, be linear, nor is it necessarily desired that the temperature be lowered through a range since an increasing, oscillating, or stepped value of temperature may be employed as an alternative in the practice of the invention. In step 308, various process parameters are read, including the rotational speed, %-Torque with respect to FSR, fluid temperature and test time.

In an optional step 310, the microprocessor 16 determines whether the data output interval previously input by the user has been reached. As used here, the phrase data output interval refers to a user-specified time interval for outputting viscometric data. An interval for data display may be selected, for example, to accommodate the time required for the spring to relax and equilibrate at a new set speed, so as to avoid an instantaneous determination of torque at or near the moment of speed change which could generate inappropriate graphical display events and/or spurious data. If the data output interval has not been attained, the various process parameters continue to be read (returning to step 308.) If the data output interval has been reached, the acquired data is sent (step 312) from the instrument 2 optionally to a viscometer component or external device for printing, display and/or storage.

In step 314, the microprocessor 16 determines whether the pre-set "wait time" interval has been reached, and if not the executing control algorithm returns to step 308 and the process parameters are again read. If the "wait time" interval has been reached, a determination is then made (in step 316) whether the %-Torque set point (or "target torque") has been reached. As described above, the target torque is selected based upon whether the viscosity of the fluid is increasing or decreasing. If the viscosity is increasing, a target torque near the upper end of the FSR (e.g., 90%) is appropriate, while a target torque set point near the lower end of FSR is more appropriate if the fluid viscosity is decreasing during the testing. Until the target torque is reached, test process control will return to step 308 in order that more data may be acquired. This particular "wait time" also accommodates the time required for the spring to relax and equilibrate at the new speed, so as to avoid successive speed shifts too close in time to another; such improper shifts may cause data to be "missed" at a speed that is, in effect, skipped over.

When the target torque has been achieved, data is output (step 318) and then another determination is made (step 320) whether one or more process parameter test end points (e.g., overall test time, fluid target temperature, number of speed changes effected and counted by microprocessor 16, detection of a static final viscosity, upper limits of the viscometer's capabilities, etc.) previously entered by the user (or programmed as part of the algorithm logic) have been reached. If such test end points are reached, the control logic ceases testing (step 322). In step 320, if the one or more end points are not reached, testing is to continue and the control logic automatically changes (through motor driver/controller 40) the rotational speed to a new constant rotational speed and returns to step 308 to begin acquiring data at the new speed. The testing will continue in this fashion until the one or more testing end points are reached.

In the increasing-viscosity example described above, the speed is reduced automatically by a decade (e.g., a factor of 10) to ensure on scale readings well within the full scale range of the viscometer. The measured torque drops and the viscometer's spring re-equilibrates at the lower speed. During this period of re-equilibration, readings may not be truly accurate, but this effect can be compensated for by properly timing and/or delaying the data acquisition following a speed change.

EXPERIMENTS

A Brookfield DV-II+ Programmable viscometer was employed using the range-extending method of the invention executed via an software-coded algorithm implemented within the Brookfield programming language. In each of the experiments described below, the viscometer was started at a rotational speed of 100 rpm, and then the speed was decreased in decade jumps: 100, 10, 1, 0.1 and finally 0.01 rpm. Thus four decades of coverage were provided, throughout which the apparent viscosity of fluids undergoing state changes were measured and recorded automatically. An additional decade of viscosity is measured and recorded, when one considers that the experiment starts under conditions (of spring range, spindle and speed) such that the initial torque at 100 rpm is 10% FSR.

Example One

A thermoreversible gel comprising KRATON® 1650 (GLS Corp., McHenry, Ill.), which is a styrene-(ethylene/butylene)-styrene triblock copolymer, and Paratherm LR™ (Paratherm Corp, Conshohocken, Pa.), a hydrocarbon liquid heat transfer fluid, was monitored during cooling from 100° C. to approximately 40° C. A Wingather™ program written by the inventor was downloaded from a personal computer or "PC" to the DV-II+ Programmable viscometer. Wingather™ was run on a PC in a "Collect All Data" mode, while the control program was run from the DV-II+ memory so that data were output through the serial or RS-232 port to the PC. The sample material was tested using a Brookfield SC4-21 spindle in a disposable sample chamber, with a Brookfield Thermosel™ heater and Programmable Temperature Controller. The polymer was dissolved into the solvent at 100° C. and subsequently cooled in steps to about 40° C., to cause gelation.

The various testing measurements acquired during testing are present in FIGS. 4A–4E.

Example Two

Figure 5A:
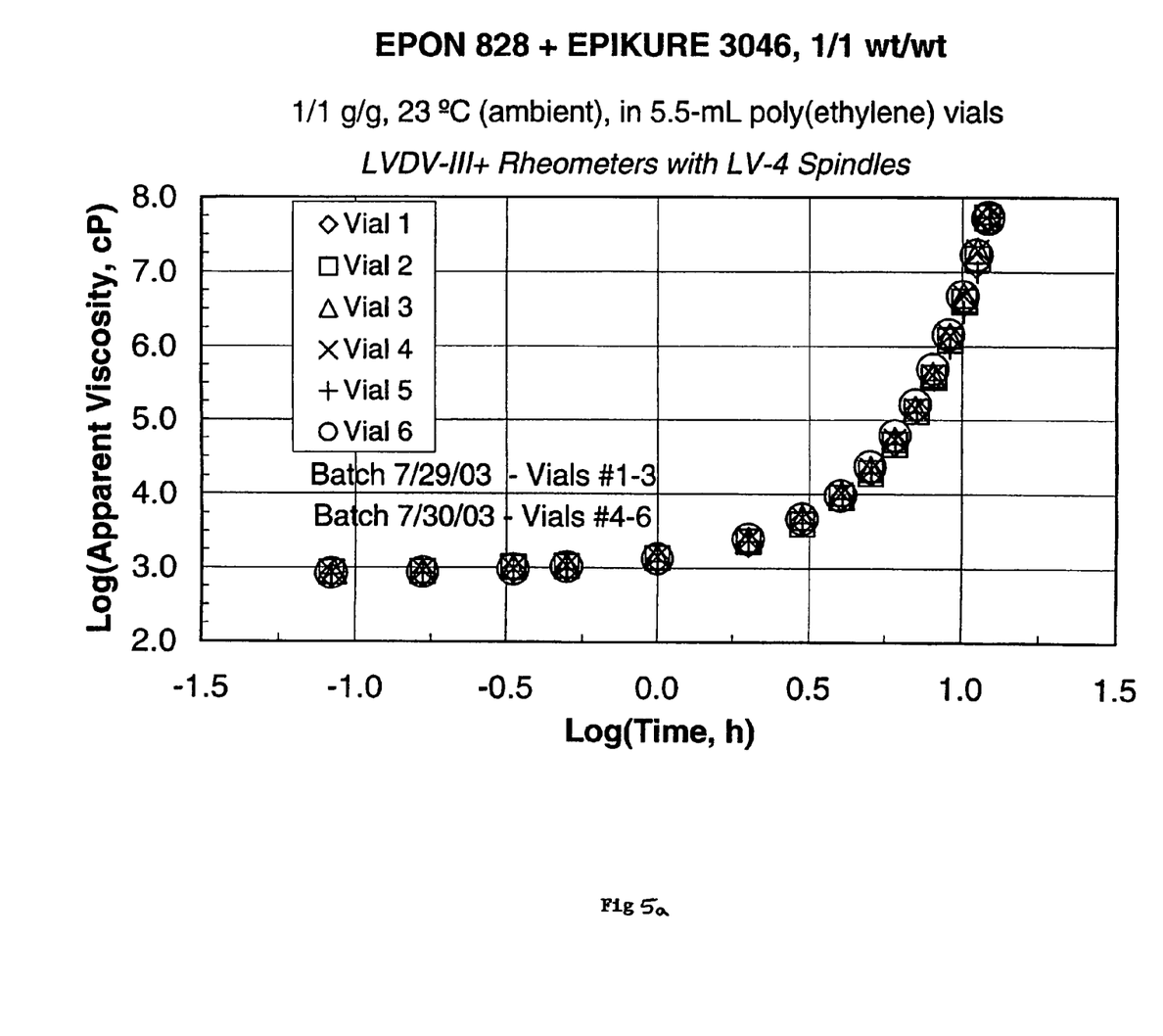
FIGS. 5A–5B are graphical representations of data acquired during the testing of another fluid sample per a method in accordance with an embodiment of the invention.

A mixture of 1/1 wt w/wt EPON™ resin 828 and EPIKURE™ 3046 was tested as it underwent chemical gelation. EPON is an epoxy oligomer (of Bisphenol A and Epichlorohydrin) and EPIKURE is an amidoamine (mixture) curing agent. Both substances were obtained from Resolution Performance Products (Houston, Tex.). The mixture was studied at 23° C., 50° C. and 60° C. The 23° C. (ambient conditions) chemical gelation or cure was analyzed using Brookfield LVDV-III+ rheometers, LV-4 spindles with Quick Connects, and 5.5-mL polyethylene sample vials. Some 23° C. samples were tested with rheometers run in stand-alone mode, using Rheoloader™ programs previously downloaded and stored in the rheometers' memories. The data were output to dot-matrix line-printers through the instruments' parallel ports. Other 23° C. experiments were performed using a Rheocalc™ program that provided PC control of the rheometer and data acquisition. Apparent viscosities measured during one 23° C. cure experiment ranged from approximately 8.70e2 to 5.40e7 cP. Data superimposibility indicated good repeatability of data for different reaction mixtures prepared with similar stoichiometry. Viscosities measured at approximately 1e4 sec differed by 0.6%, for example. Data for all 23° C. tests are shown in FIG. 5A.

Figure 5B:
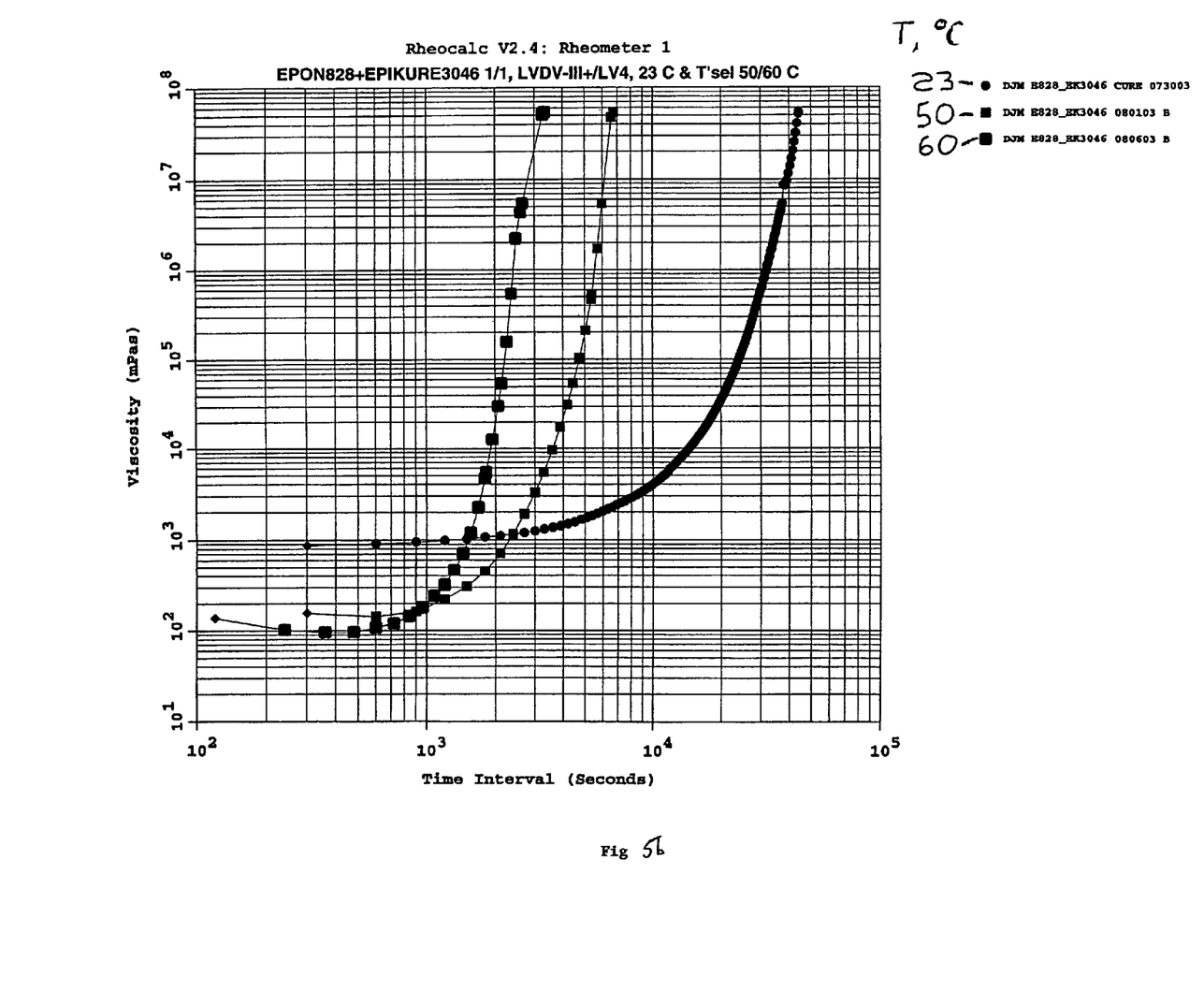
Figure 6A:
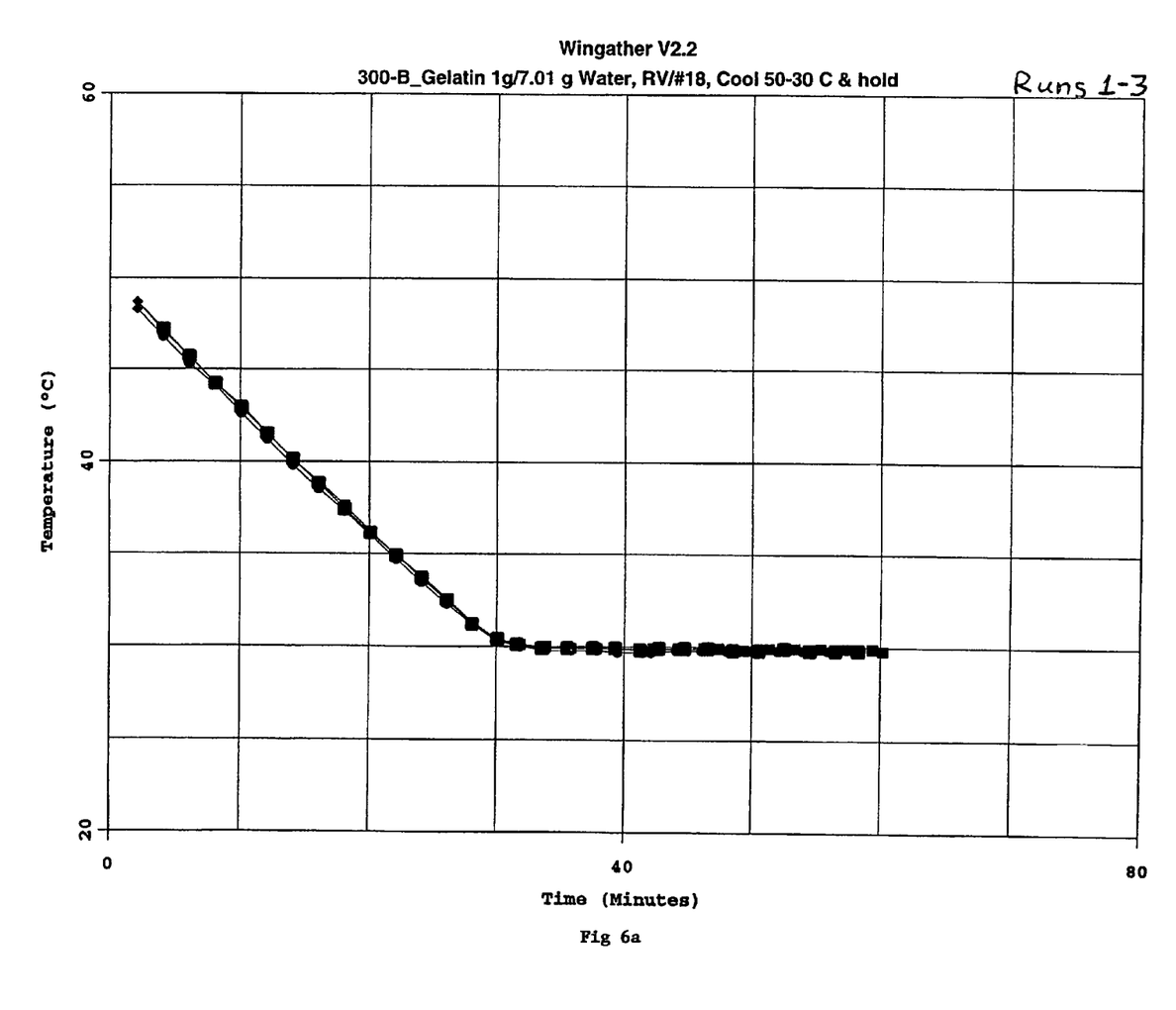
FIGS. 6A–6D are graphical representations of data acquired during the testing of yet another fluid sample per a method in accordance with an embodiment of the invention.
Figure 6B:
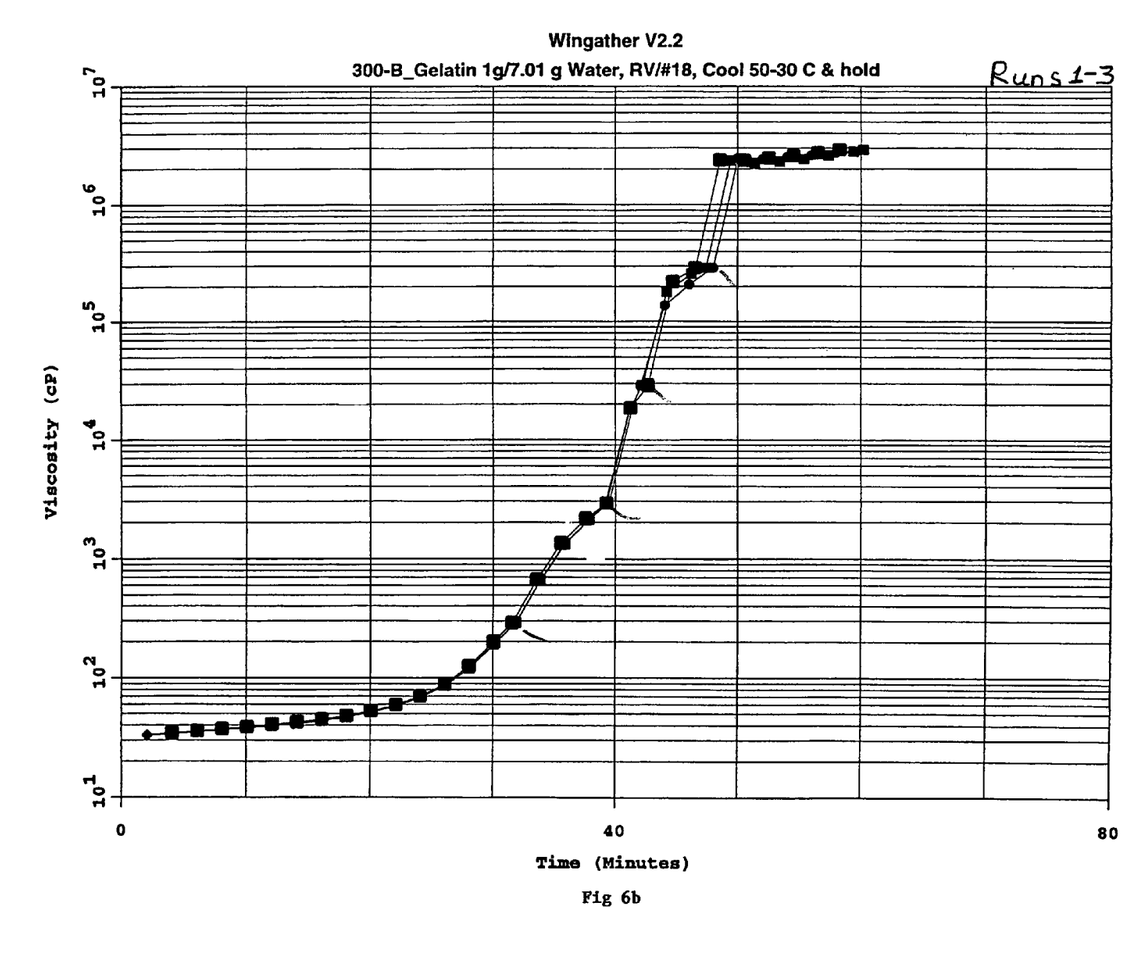
Figure 6C:
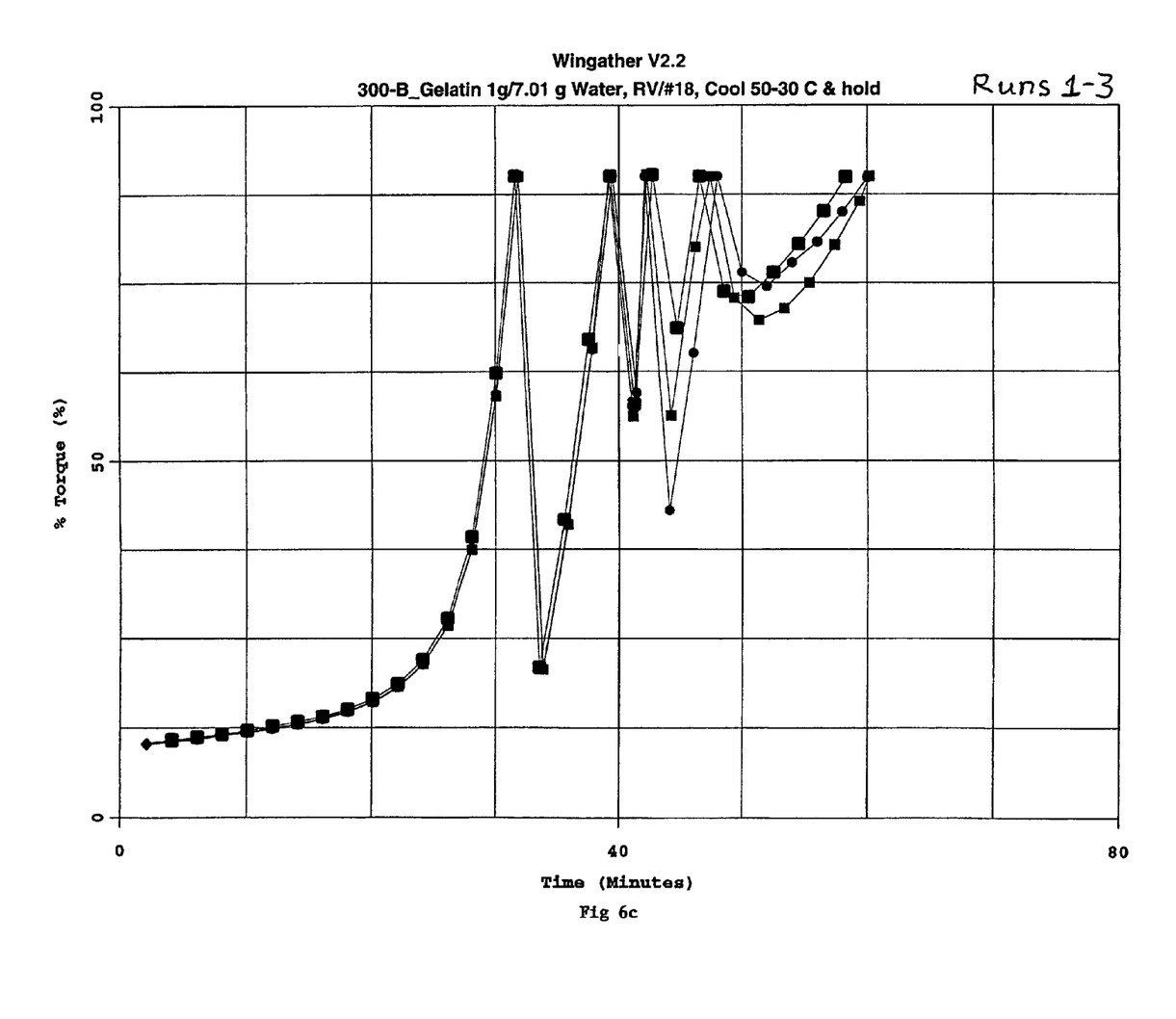
Figure 6D:
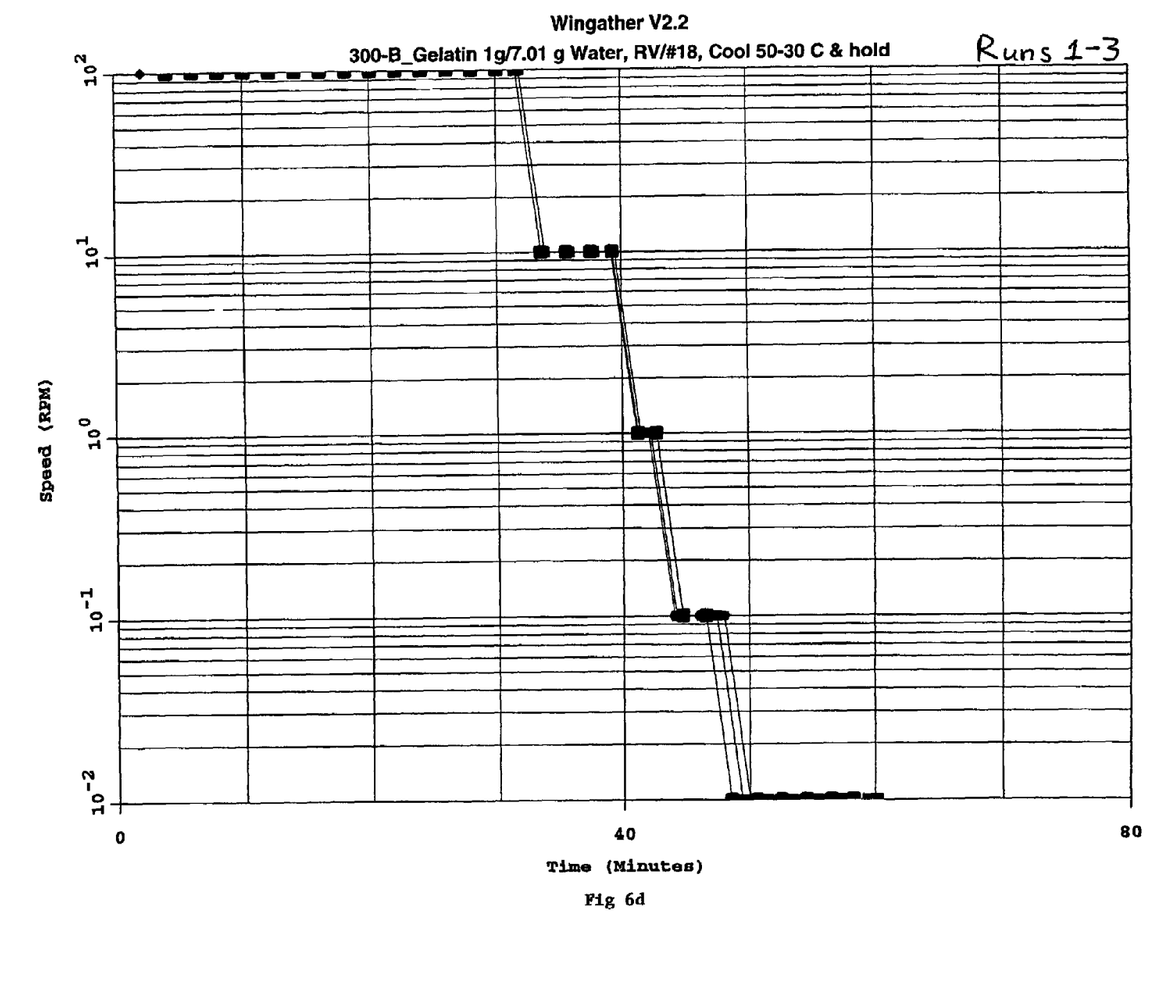

The gelation at (1) 50° C. and (2) 60° C. was studied using LVDV-III+ rheometers, LV-4 spindles with Quick Connects, Brookfield Thermosel™ heater and Programmable Temperature Controller, and Disposable Sample Chambers. Rheocalc™, run on a PC, provided instrument control and data acquisition. A comparison of representative data collected at 23, 50 and 60° C. is shown in FIG. 5B.

Example Three

Aqueous 300-Bloom (porcine) gelatin (Aldrich Chemical Co, Milwaukee, Wis.) was dissolved in water for 30 minutes at 50° C., and was studied during cooling from 50° C. to 30° C. A Wingather™ program written by the inventor was downloaded from a personal computer or "PC" to a RVDV-II+ Programmable viscometer. Wingather™ was run in "Collect All Data" mode, while the program was run from the DV-II+ memory so that data were output through the serial or RS-232 port to the PC. The material was tested using a Brookfield Small Sample Adapter, SC4-18 spindle, SC4-13RPY sample chamber with integral temperature probe, and TC-501P bath for temperature regulation.

Test results are presented in the graphs of FIGS. 6A–6D.

CONCLUSIONS:

The test results demonstrate that extended-range viscosity measurements can be reliably performed over four to five decades using comparatively low-cost viscometers modified to execute the method steps described above. It was not apparent or otherwise obvious prior to the present invention that such reliable viscosity data could be so obtained economically in contrast to single-decade conventional testing. Testing has established validity of the present method and implementing apparatus. Repeatability appears to be satisfactory between similar-condition test runs performed with a given aliquot.

At extremely low rpm, an artifact "peak" in viscosity upon speed change may be detected if the data output rate is fast compared to the instrument's spring equilibration time, given the extremely high viscosity sample's slow relaxation. Increasing the data output time interval will allow the now slowly rotating spring more time to mechanically equilibrate at the new speed before more data are output It will now be apparent to those skilled in the art that other embodiments, improvements, details, and uses can be made consistent with the letter and spirit of the foregoing disclosure and within the scope of this patent, which is limited only by the following claims, construed in accordance with the patent law.

What is claimed is:

1. Method for measuring a physical property of a fluid undergoing a state change, comprising the steps of:
   (a) providing a rotary viscometer instrument having a rotor assembly including a spindle, a chamber in which the fluid is to be contained, means for adjustably driving the rotor assembly, means for measuring torque imparted to the spindle and converting the measured torque to a viscosity measurement;
   (b) placing a fluid to be tested in the chamber;
   (c) placing the spindle in contact with the fluid;
   (d) rotating the rotor assembly at a constant rotational speed;

(e) measuring torque imparted to the spindle by the fluid and converting the measured torque to a viscosity measurement until at least one torque set point is reached;

(f) determining if at least one process parameter has reached a predefined end point, and if the at least one process parameter has not reached the end point, dynamically changing the rotational speed of the rotor assembly to a different constant speed; and (g) repeating steps (e) and (f) until the at least one process parameter reaches the predefined end point.

2. The method of claim 1, wherein the at least one torque set point is selected as a percentage of the instant full scale range of the viscometer instrument.

3. The method of claim 1, wherein dynamically changing the rotational speed comprises decreasing the rotational speed to a lower constant rotational speed.

4. The method of claim 3, wherein the torque set point is approximately 90% of the instant full scale torque measurement range of the viscometer instrument.

5. The method of claim 4, wherein the lower constant rotational speed is a decade lower than the constant rotational speed being dynamically changed.

6. The method of claim 1, wherein dynamically changing the rotational speed further comprises increasing the rotational speed to a higher constant rotational speed.

7. The method of claim 6, wherein the torque set point is approximately 10% of the instant full scale torque measurement range of the viscometer instrument.

8. The method of claim 7, wherein the higher constant rotational speed is a decade higher than the constant rotational speed being dynamically changed.

9. The method of claim 1, wherein the measuring step further comprises taking a torque a measurement at preselected time intervals.

10. The method of claim 1, wherein the torque measurements are delayed immediately following each rotor assembly speed change to allow equilibration to occur at each different constant speed.

11. The method of claim 1, wherein the at least one process parameter comprises the measured torque and the process end point is defined in terms of the capabilities of the viscometer instrument.

12. The method of claim 1, wherein the process end point comprises a predefined number of rotational speed changes.

13. The method of claim 1, further comprising the step of measuring the fluid temperature, and wherein the process end point comprises a target temperature.

14. The method of claim 1, wherein the process end point comprises a time period starting from the initiation of torque measurements.

15. The method of claim 1, wherein the process end point comprises a torque measurement that is substantially static over a selected time interval.

16. In a rotary viscometer instrument, which includes a rotor assembly including a spindle and a chamber in which a fluid undergoing a state change is to be maintained in contact with the spindle or an extension thereof, means for measuring torque imparted to the spindle and converting it to a viscosity, and means for variably driving the rotor assembly at constant rotational speeds, an improvement which comprises:

means for selecting at least one torque set point; and
means for dynamically changing the rotational speed of the rotor assembly when the at least one torque set point is reached as detected by the instrument.

17. The rotary viscometer instrument of claim 16, wherein:
the means for selecting the at least one torque set point further selects at least one testing end point;
means for determining if at least one process parameter has reached the at least one testing end point.

18. The rotary viscometer instrument of claim 17, wherein the at least one process parameter comprises the measured torque and the at least one testing end point is defined in terms of the capabilities of the viscometer instrument.

19. The rotary viscometer instrument of claim 17, further comprising:
means for counting the number of speed changes occurring; and
wherein the testing end point comprises a predefined number of speed changes.

20. The rotary viscometer instrument of claim 17, further comprising:
means for measuring the fluid temperature; and
wherein the at least one testing end point comprises a target temperature.

21. The rotary viscometer instrument of claim 17, further comprising:
a timer; and
wherein the at least one testing end point comprises a time period starting from the initiation of torque measurements.

22. The rotary viscometer instrument of claim 17, further comprising:
a timer; and
wherein the at least one testing end point comprises a torque measurement that is substantially static over a selected time interval.

23. The rotary viscometer instrument of claim 16, wherein the at least one torque set point is selected in terms of a percentage of the instant full scale range of the viscometer.

24. The rotary viscometer instrument of claim 16, wherein the means for dynamically changing the rotational speed of the rotor assembly further comprises a motor speed controller.

25. The rotary viscometer instrument of claim 16, wherein the rotor assembly rotational speed changing means changes the rotational speed in decades.

26. The rotary viscometer instrument of claim 16, further comprising:
means for taking torque measurement at pre-selected time intervals.

27. The rotary viscometer instrument of claim 26, further comprising:
means for delaying the measurements immediately following each rotor assembly speed change to allow equilibration to occur at each different constant rotational speed.

28. The rotary viscometer instrument of claim 16, wherein the viscometer instrument comprises a Brookfield viscometer or rheometer.

* * * * *